United States Patent
Berlanga Acosta et al.

(10) Patent No.: US 7,465,704 B2
(45) Date of Patent: Dec. 16, 2008

(54) METHODS FOR ENHANCING HEALING OF DIABETIC FOOT ULCERS BY INJECTING EPIDERMAL GROWTH FACTOR (EGF)

(75) Inventors: Jorge Berlanga Acosta, Playa, Ciudad de la Habana (CU); José I Fernández Montequin, Amargura 318 entre Aguacate y Compostela, Habana Vieja, Ciudad de la Habana (CU); Calixto Valdés Pérez, Playa, Ciudad de la Habana (CU); Neobalis Franco Pérez, Marianao, Ciudad del al Habana (CU); Ingrid Rojas Constantin, Playa, Ciudad de la Habana (CU); Héctor Santana Milián, Playa, Ciudad de la Habana (CU); Larissa Chacón Corvea, Playa, Ciudad de la Habana (CU); Gerardo E. Guillén Nieto, Plaza de la Revolución, Ciudad de la Habana (CU); Luis Herrera Martínez, Playa, Ciudad de la Habana (CU); Leonardo Canan-Haden Frías, Playa, Ciudad de la Habana (CU); Haydee Gerónimo Pérez, Playa, Ciudad de la (CU); Jorge Sotolongo Pena, Playa, Ciudad de la (CU)

(73) Assignee: Centro de Ingeniera Genetica y Biotecnologia, Cuidad de la Habana (CU)

( * ) Notice: Subject to any disclaimer, the term of this patent is extended or adjusted under 35 U.S.C. 154(b) by 237 days.

(21) Appl. No.: 10/499,457

(22) PCT Filed: Dec. 4, 2002

(86) PCT No.: PCT/CU02/00011

§ 371 (c)(1), (2), (4) Date: Jan. 7, 2005

(87) PCT Pub. No.: WO03/053458

PCT Pub. Date: Jul. 3, 2003

(65) Prior Publication Data

US 2005/0107294 A1   May 19, 2005

(30) Foreign Application Priority Data

Dec. 20, 2001   (CU) .................... 0308/01

(51) Int. Cl.
*A61K 38/18* (2006.01)
*C07K 14/485* (2006.01)
(52) U.S. Cl. .................... 514/12; 530/399
(58) Field of Classification Search .............. None
See application file for complete search history.

(56) References Cited

U.S. PATENT DOCUMENTS 5,130,298 A * 7/1992 Cini et al. ............ 514/12
6,696,238 B2 * 2/2004 Murphy et al. ........ 435/1.1

FOREIGN PATENT DOCUMENTS

EP   0 312 208 A   4/1989
WO   90 01331 A   2/1990

OTHER PUBLICATIONS

Brown G. L. et al., "Stimulation of Healing of Chronic Wounds by Epidermal Growth Factor", *Plastic and Reconstructive Surgery* (1991), 88(2):189-194.
Brown G. L. et al., "Enhancement of Epidermal Regeneration by Biosynthetic Epidermal Growth Factor", *The Journal of Experimental Medicine* (1986), 163(5):1319-1324.
Hogge J. et al., "The Potential Benefits of Advanced Therapeutic Modalities in the Treatment of Diabetic Foot Wounds", *J. American Podiatric Med. Assoc.*(2000), 90(2):57-65.
Zhu Xier et al., "Studies on Enhancing the Repair of Gangrenous Skin Diabetic Foot by Epidermal Growth Factor", 5th *China-Japan Symposium on Diabetes Mellitus* (1997), 1141:241-243.
English Translation of Zhu et al., "Clinical Studies on Enhancing the Repair of Gangrenous Skin of Diabetic Foot by Epidermal Growth Factor," *Natl. Med. J. China.*, 1996, 76:862.

* cited by examiner

*Primary Examiner*—Marianne P Allen
(74) *Attorney, Agent, or Firm*—Hoffman & Baron, LLP

(57) ABSTRACT

The invention relates to the use of Epidermal Growth Factor (EGF) in a preferably-injectable pharmaceutical composition which is administered by means of infiltration into and around chronic cutaneous ischaemic lesions in order to prevent diabetic foot amputation. Said composition can be administered to recently-created surgical surfaces damaged by the effect of acute reperfusion with oxygenated blood following prolonged ischaemia, thereby preventing further surgical procedures and favouring the preservation of the extremity. The aforementioned composition can be used to improve (i) the cell microenvironment, thereby increasing the reparative and defensive capacity and viability of the is tissues and (ii) the cicatrisation of cutaneous ischaemic lesions, thereby stimulating cell proliferation. The invention is suitable for use in human, veterinary and experimental medicine, specifically in vascular angiology and surgery, dermatology, burn treatment and reconstructive surgery and geriatric medicine. Said composition can be used for recalcitrant ulcers which are associated with lesions in the macro and/or microvasculature, patients with inadequate lymphatic and/or venous return and ulcers or other lesions which are difficult to cicatrise and/or heal.

19 Claims, No Drawings

METHODS FOR ENHANCING HEALING OF DIABETIC FOOT ULCERS BY INJECTING EPIDERMAL GROWTH FACTOR (EGF)

This application is the U.S. National Phase of International Application Number PCT/CUO02/00011 filed on 4 Dec. 2002, which is incorporated herein by reference.

TECHNICAL BRANCH

This invention deals with the use of a pharmaceutical composition, which contains Epidermal Growth Factor (EGF), preferably in an injectable form and to be administered through infiltrations inside and around cutaneous chronic ischemic ulcerative wounds as to prevent diabetic limb amputation. It may be administered on recently induced surgical post-amputation surfaces, or damaged by the process of acute reperfusion with oxygenated blood, following prolonged ischemia. This allows for the prevention of surgical re-interventions, thus assisting in limb preservation.

PRIOR ART

Every organ and tissue of the body is susceptible to suffer irreversible damages following partial or complete, acute or chronic arterial blood supply suppression. Tissue damages might also occur as a consequence of chronic venous drainage failure (T. D. Lucas y I. L. Szweda. Cardiac reperfusion injury: aging, lipid peroxidation and mitochondrial dysfunction. Proc Natl Acad Sci USA 1998, 95 (2): 510-514). All these disorders are largely frequently found in Diabetes Mellitus affected patients. In these individuals limbs local circulation might fail due to macro and microvascular deteriorum. Furthermore, peripheral nerves structures are also affected which also contributes to the circulatory deterioration. Diabetes-associated damages to the autonomic or sensitive innervations systems ensues the failure of limb's skin defense mechanisms as sweating and sebaceous gland secretion. Local insensibility renders the foot prone to local traumas which might evolve to a problem wound.

A variety of risk factors have been associated with the difficult-to-heal seen in diabetic patients, i.e., high and sustained glycemia, glycosilation of hemoglobin and of many other circulating and tissue proteins, i.e., collagen, etc (Kurose I, Argenbright L W, Wolf R, Lianxi L, Granger D N. Ischemia/reperfusion-induced microvascular dysfunction: role of oxidants and lipid mediators. Am J Physiol 1997, 272: H2976-H2982). As a result of this healing deficit that is further complicated by the circulatory disturbances, many diabetic patients undergo limb amputation. Patients with inflammatory or degenerative arteriopathies of the limbs frequently exhibit negligible or null perfusion below the knees join. This sustained hypoxic scenario renders other cutaneous, microvascular, nervous and joins complications, while the former often leads to a recalcitrant to treatment ischemic ulcer. Besides, nerves, vessels, and other cutaneous structures may become severely deteriorated and often they succumb. This further sustains the propensity to recalcitrant ulcers. (McCallon S K, Knight C A, Valiulus J P, Cunningham M W, McCulloch J M, Farinas L P. Vacuum-assisted closure versus saline-moistened gauze in the healing of postoperative diabetic foot wounds. Ostomy Wound Manage 2000, 46:28-32).

Here we will describe some solutions currently used today in the medical arena to afford this affliction.

Among the general procedures used in the art today, the metabolic balance correction allows for the reduction of risk factors of diabetic complications. In addition, off-loading of the affected limb is a well-focused solution to facilitate limb ulcer healing. Antibiotics administration and frequent surgical debridements of necrotic and fistulized tissues are in the current state of the art. These may be conducted irrespective of the perfusion of the infected foot. However, for severe and recalcitrant cases of serious ischemic and progressive ulcers, amputation is irreversible. Other medical adjunctive interventions for either chronicity or rebounds are used in the art today having shown some benefits.

Haemorrehologic therapy: the rationale of this therapy is based on the well-known haemorrehologic disturbances found in the blood of diabetic patients, which at the same time might increase the opportunistic infection risk.

Vasoactive therapy: this intervention has been used to alleviate the perfusion deficits due to the macro and microangiopathy. Some prostanoids have shown to be of benefit at the affected tissue level.

The use of any of these therapeutic interventions demand however, a prior examination of a number of functional systems, such as cardiovascular, renal, hepatic, etc, which might be found impaired in diabetic patients, particularly, the first and the second ones. Under certain conditions, other therapies have been introduced as to prevent or correct platelet aggregation as well as thrombolytic agents.

Surgical procedures for major revascularization are always risky for any ischemic patient, whether diabetic or not. Besides, these are expensive, and not applicable to many patients. Its indication is therefore very limited. Endovasacular surgery is also complex, expensive, and has provided a limited applicability for arterial sectors such as aorto-iliacus and femoro-popliteus. Most often these sectors appear calcified while lesions appear in a patched fashion.

Lumbar sympathectomy is today exceptionally practiced in diabetes. The existence of a previous autonomic neuropathy hinders its usefulness.

A recently emerged hope to deal with the diabetic foot wounds is the human recombinant platelet derived growth factor, commercially known as Becaplermin or Regranex, which has been approved by the Food and Drug Administration (FDA) of the USA. This medication is particularly indicated for neuropathic foot ulcers. The most recently published data indicate only a 50% of efficacy in a multicenter, controlled, and randomized clinical trial in the USA (T. Jeffery Wieman, Janice M. Smiell, Yachin Su. Efficacy and safety of topical gel formulation of recombinant human platelet derived growth factor—BB (Becaplermin) in patients with chronic neuropathic diabetic ulcers. Diabetes Care 1998, 21: 822-827). It is remarkable that the wounds medicated with Becaplermin in the aforementioned study PDGF-BB are small and shallow and that by no means may be compared in size or severity with those we have treated along our invention. On the other hand the clinical trial is conducted on neuropathic foot ulcers with a normal and standard arterial blood supply. In our case, severe ischemic ulcers referred as in stages IV and V according to Wagner classification have been treated and healed. Most of the wounds we have managed are ischemic. All the wounds we have treated are bigger than 20 $cms^2$ and from 10 to 40 mm depth. In the PDGF-BB clinical trial wounds involve only about $2.7 \pm 3.45$ $cms^2$ and $0.5 \pm 0.49$ cms in depth. A critical aspect to be solved by PDGF-BB therapy is the high rate of recurrence. This is about 30% in the third month.

Another recent invention for large acute cutaneous wounds, such as burns, or chronic as venous ulcers, has been the creation of bioartificial human skin equivalents. Yet, controlled clinical trial on diabetic foot ischemic ulcers are missing and it seems unlikely that any of the human skin equivalent could control or reverse the underlying ischemic process (Editorial. New Skin for Old. Developments in Biological Skin Substitutes. Arch Dermatol 1998; 134: 344-348).

In general terms there is no medical treatment having shown to be efficacious in healing such kind of wounds, which recalcitrant behavior is associated to the local ischemia. Preventing recurrence may turn in an even more complex challenge.

SPECIFICATIONS

DETAILED DESCRIPTION OF THE INVENTION

The object of the invention herein described is the use of an injectable pharmaceutical composition containing Epidermal Growth Factor (EGF) that enhances tissue survival and adaptation to hipoxia; which allows for the healing of cutaneous ischemic and chronic ulcers of skin and adjacent soft tissues in an irreversible manner. The composition allows for the healing of ischemic ulcerative or not type wounds or those wounds exposed to and damaged by the process of reperfusion with arterial blood on the skin and sift adjacent tissues. It is defined the ischemic wound in this context as that of skin and soft tissues of the lower limb as a result of a failure in the peripheral perfusion due to a long term damage of large and small vessels in a diabetic patient. The wounds affected by the reperfusion process are mostly created upon amputation or sharp debridement when the oxygenated blood supply is reinitiated following prolonged periods of territorial hemodynamic perfusion silence. Alternatively, these processes may appear following revascularization surgical procedures in diabetic patients.

The use of EGF in these lesions attenuates the progressive tissue deterioration, particularly in the legs and the feet associated to blood flow failure and toxin storage in the tissues.

The composition of the invention has shown to trigger and steadily sustain the process of healing in chronic ischemic wounds in which the current art therapy has been unsuccessful. By using this composition limb amputation is unnecessary when there are no other medical choices available for the ischemic and chronic wound. The composition has proved to be useful as well in reducing the damages associated to surgical reperfusion allowing for the complete healing of ulcers in ischemic/infected/neuropathic feet. The process of cellular arrest on the wound edges and the subsequent tissue fading are overtly aborted with this therapy. This excludes the need for further and progressive sharp debridements and partial amputations. The composition by mean of a generally cytoprotective and rescue effects enhances the healing of ischemic/infectious/neuropathic diabetic foot ulcers.

The composition is applied by mean of local infiltration within the wound margins and bottom of the lesions, and might contain the polypeptide obtained by natural, recombinant or synthetic technologies. The administration procedure is like a local anesthetic blockade inserting the needle in different point into and around the lesion, so that all the deep bottom surface and edges are flushed with the composition. The composition is deposited into 4 to 20 infiltration points so that in between each point the distance must be no longer that 1,5 cms. The number of points to be covered is according to that skilled in the art. Such wounds with bigger size will require a larger number of instillation points. The skilled in the art will perceive a couple of well recognized effects on the administration time: local edema and local resistance to the composition flushing. Sharp debridement of wound edges and bottom will be according to the experience of the skilled in the art. In general terms sharp debridements and minor amputations are significantly reduced upon treatment progression. If along the treatment period edges become atonic, they can be conservatively debrided and later infiltrations are to be carried out in a sub-epithelial space. Infiltrations are usually conducted on alternate days of a week so that in each week three infiltration sessions are conducted. The number of infiltration points in each session depends upon the size of the wound, ordinarily ranging between 4-20. In infectious/ischemic wounds as in stages IV and V according to Wagner's classification the outbreak of granulation tissue is following the sixth infiltration session. In less severe wounds, it is possible to see some response since the first week of treatment, so after three infiltration sessions. Alternatively, in very severe ischemia associated to total deficit of peripheral beat and anemia below 9 g/L the treatment has been used under daily bases. In these patients granulation evidences are imitated around the ninth session of infiltration. In all the cases the total volume to inject is about 1 milliliter, so that an ulcer may receive a total volume of 4-20 mL of the composition. It is preferably the use of hypodermic needles 27½. The composition may contain the EGF polypeptide obtained from a natural source, via chemical synthesis or by mean of recombinant DNA technology. The use of the pharmaceutical composition containing EGF described herein has permitted the complete tissue regeneration of chronic and ischemic lesions whereas the procedure is minimally invasive. The use of the composition has also reduced the number of surgical interventions and the number of minor or major amputations. In other cases, the use of the herein described invention has allowed (I) removal of ischemic capsules with no need for surgical procedures. This is probably due to the emergence of a new remodeling granulation tissue from deep zones, which pushes up and detaches the necrotic material. (II) The growth of a new intra cutaneous fibroangiogenic tissue, consequent to successive infiltrations, before going to amputation as for examples in toes, so that there is a previous pro-granulating environment. This contributes to limit and to abort the septic complications, enhances wound healing and attenuates the reperfusion damages.

The components of the pharmaceutical composition are as follows:

Epidermal growth factor (EGF): Cytoprotective agent that allows for the activation of cellular self-defense mechanisms when administered into the ulcer. EGF promotes adaptation and survival rescue of cells within stressful conditions. EGF triggers is apoptosis in aged fibroblasts as those damaged and/or aged, and acts as a survival factor to others that are eventually rescued. EGF plays a selective pressure within the microenvironment, where adapted cells are committed to proliferate. Due to its cytoprotective effect, ischemia/reperfusion damages are prevented. The composition contains 10-1000 micrograms/ml of sterile vehicle. EGF may be natural, synthetic or recombinant. EGF may be in liquid form, suspended in water, in solution with a buffer, freeze-dried to be dissolved, etc. EGF may be as a powder of fine granulate, and to be applied by mean of high pressure shooting device. EGF may be administered as in its DNA form within a proper genetic construct suitable for its expression transiently transfected human cells.

Polyethyleneimine (PEI): This is highly positively charged—protonated chemical compound that enhances the interaction of EGF with its receptor, prolongs its half life in the extracellular matrix and prevents its intracellular degradation, so that in this way its biological effects are amplified. It may be found in the formulation in a molar relation of 1:1 with EGF up to 1 (EGF): 10 (PEI).

Sodium Phosphate Buffer: Chemical stabilizer. Its pH is about 6.5 and in a molar range concentration of 5-100 mM. The optimal range in the formulation is 10-20 mM.

O-Raffinose: Stabilizing agent for the freeze drying process. Concentrations of 5-50 mg/ml can be used whereas its optimal rage is 8-20 mg/ml.

L-Glycine: Isotonizing agent. Concentrations of 5-50 mg/ml can be used whereas its optimal rage is 10-20 mg/ml.

Fibronectin: Promotes the stability of EGF as its biological functioning. It promotes the interaction between EGF and its cellular receptors. It is in a range from 10-20 mcg/mL.

Levan: This is a protecting agent for EGF when it is in solution. It acts screen agent for EGF. Facilitates its biodistribution within the extracellular space. In the composition it is found in a range from 1-20 mgs/mL.

The pharmaceutical composition might combine EGF as well with the following active principles:

Rutin: Phlebotonic and phlebotrophic. It might be present in the formulation at concentrations of 20-1000 µg/ml. It might be used as a free Rutin hydrate or as a lyophilized salt of Rutin, as in a sulphate.

Lidocaine: Trophic agent. Lidocaine contributes to attenuate the local secretion of pro-inflammatory cytokines, as the expression of adhesion molecules within the vascular lumen. In the formulation lidocaine is used as a chlorhydrate and its concentration might be present in a range of 5-40 mg/ml.

Adenosine tri-phosphate (ATP): It plays vasodilator and pro-metabolic effects. Its concentration in the formulation ranges from 0.05 to 20 mg/ml as a sodium salt or free acid.

Guanosine triphosphate (GTP): Enhances local vasodilatation. It is present in the formulation as a sodium salt. Its concentration ranges from 1 to 100 mg/ml.

Amide of the nicotinic acid (Nicotinamide): Renders useful anabolic substrates for the cells. Its concentration ranges from 1 to 130 mg/ml.

L-Arginine: Contributes to the regulation of the vascular tone. Useful in the formulation as hydrochloride crystals. Its concentration ranges from 1-100 ng/ml.

Heparin: Cytoprotective, pro-mitogenic agent. Useful in the formulation as a sodium salt, in a concentration ranging from 1 to 10 µg/ml (0.1-1 U).

EXAMPLES

A total number of 9 patients received therapy with the pharmaceutical composition. All the patients shared the following characteristics:

1. All the patients were affected by type-II diabetes mellitus, with an evolution of 10-25 years, basically treated with oral hypoglycemiants.
2. A history of difficult healing was registered for all the patients. Some patients had undergone previous contra lateral amputations.
3. All the wounds treated corresponded to diabetic limb chronic ulcers, being classified as ischemic/infectious/neuropathic diabetic foot or mixed forms. Stages IV or V according to Wagner's classification predominated for all the wounds.
4. All the wounds treated with the present formulation might be considered as recalcitrant or difficult to heal wounds; some with one month or more of age.
5. All the wounds were about or larger than 20 $cm^2$; in most case ulcers depth involved the periosteum, having bone tissue overtly exposed. Among, them a patient is included with concomitant ischemic calcaneous.
6. All the patients treated were highly prone to amputation
7. All the patients were followed after hospital discharge and none of them has recurred so far. Neither late adverse reactions nor local ischemia signs were observed. No adverse reactions have been registered upon time.

Treatment was based on deep perilesional infiltrations over at least five different and equidistant points of the wound bottom and contours. The syringe needle must always be oriented toward the central basement area of the wound bottom, to the edges and/or to tunnels when exist. On each injection point, 1 ml of solution is deposited. No unwanted reactions are observed along or next to the treatment, except the ordinary local sore. The formulation always borne EGF as main active principle, while in some instances, the formulation contained some of the above mentioned active principles. In all the patients treated toes, foot, or major amputations procedures were prevented. The total number of infiltration sessions for each patient is shown in each example.

Example 1

Patient ACDF, 49 years old, female. Patient bearing an ischemic/infectious diabetic foot, affected by type-II diabetes mellitus with an evolution of 16 years, the patient had undergone prior sympathectomy and supracondilial amputation of the right limb a couple and half years ago. The first finger of the left foot was surgically removed while showing an ulcerative, humid, atonic, and difficult-to-heal lesion despite many minor surgical debridements to remove ischemic capsules, revitalize the edges and the bottom of the wound. The amputation shaft turned ischemic, with cyanotic and atonic edges following 5 days of the surgery. The infiltration of the composition is initiated expecting spontaneous re-epithelialization of the ulcer. From the fourth infiltration it was noticed a dramatic change of the aspect of the wound, starting a productive granulation tissue, bleeding, and that after a few days it was resurfaced with epithelium. The patient received a total of 9 sessions of infiltration (3/weeks and therefore three weeks of treatment). Following re-epithelialization she was discharged from hospital. Has shows a satisfactory evolution with recurrence.

Example 2

Patient ERC, 66 years old, female. Patient with a 12 yr. evolution of type-II diabetes mellitus, bearing an ischemic infectious foot and lacking distal beatings. A minor is transmetatarsal amputation was practiced having a large tunnel downward. The base of the amputation turned cyanotic, ischemic, atonic, and with large deposit of a yellow component. The infiltrations are begun with the expectance of producing granulation tissue and a spontaneous second intent healing. The wounded foot had completely healed, granulated and resurfaced with epithelium, including the tunnel after 11 infiltration sessions. It included a lateral tunnel of about 4 cms In depth. Evidences of scar remodeling are observed in this patient for the first time.

Example 3

Patient ECS, 63 years old, female. Patient type-II diabetes mellitus since she was 41 years old. She is bearing an ischemic infectious foot and with a previous contralateral infra-condilial amputation. She is admitted to receive amputation of her first toe due to severe ischemia. Upon surgery an ischemic capsule is implanted on the base of the next toe that extended back and downward. At this point the lesion is atonic, and no healing progress is observed. Fingers and adjacent soft tissues are removed, opening a large and deep edge, resembling a 6 cms length tunnel. Ischemic and necrosis signs recurred on day 3 post-surgery. Wound contours turn cyanotic and ischemic three days later. The composition infiltrations are initiated expecting a second intent healing response. Complete healing was achieved following 11 sessions when the patient had fully re-epithelialized the wound with well-keratinized epithelium. The patient was discharged from hospital. Scar remodeling was also observed.

Example 4

Patient RNP, 69 years old, male. A patient with a 12 yr. old evolution of type-II diabetes, with distal beatings deficit, bearing an ischemic/infectious foot. The patient undergoes a transmetatarsal amputation due to ulcerative lesions, recalcitrant to heal with current art therapy. On the surgical area ischemic plaques were onset and the healing process did not show to progress any longer. Patient complained of spontaneous pain on bed. The cyanosis extended around the surgery contours and there was negligible bleeding during debridements. The ischemic plaques were surgically removed, and on day $4^{th}$ post-surgery infiltrations therapy were initiated. Evidences of tissue improvement were observed on day 6 post-infiltration, so that spontaneous pain disappeared, and being overtly expressed a red granulation tissue. Following 12 infiltration sessions, the patient had completely re epithelialized the wound, so it means 4 weeks of treatment. He was discharged from hospital and has evolved well with no recurrence upon a 12-months follow up.

Example 5

Patient ISV, 74 years, female. Patient afflicted by diabetes since 30 years ago. She is bearing an ischemic/infectious foot. There is a previous transmetatarsal amputation and a history of deficit of healing. She is admitted due to necrotic lesion of the $5^{th}$ toe. The surgery is practiced and ischemic plaques appear over the next few days. She received further debridement and an external extensive edge is opened with exposed periosteum in the inferior and external side of the foot. The edge became ischemic over the next 48 hours, thus, the infiltration therapy is introduced trying to achieve a spontaneous second intent heal, including the edge. After the $6^{th}$ infiltration a useful and bleeding granulation tissue arises. The lesion favorably responded to the treatment and was fully epithelialized following 11 sessions. The patient has had a satisfactory evolution following hospital discharge.

Example 6

Patient RDR, 44 years old, male. A patient affected by type-II diabetes since 12 years ago. He bears an ischemic/infectious diabetic foot that due to ischemic lesions on two toes receives transmetatarsal amputation. The patient lacks distal beatings and shows clinical evidences of insufficient peripheral perfusion. He has a history of healing failure on the contralateral tibial region. Following amputation cyanotic foci appeared on the cutaneous contours of the wound. The infiltration is begun with the expectance of rendering sufficient granulation tissue to host an auto-graft, or to heal and remodel by second intent. On the $4^{th}$ infiltration the first sprouts of granulation tissue appear and reanimation of the wound edges, which also were normochromic and hypertrophic. The auto-graft was unnecessary. By carrying out 15 infiltration sessions (5 weeks) there was no required to make a self auto-grafting. Upon hospital discharge has had a successful evolution.

Example 7

Patient RGR, 49 years old, female. This is diabetes patient since about 10 years with painful claudicating along 100 meters walk and difficult to heal histories. She has had several recalcitrant ulcers on the paratibial area of both limbs. The lesion to be treated is an ischemic ulcer on the lower third of the left leg on its lateral external side with approximately 6.4 cms of diameter and 0.5 cm depth. The ulcer has progressed for two months with no healing. The first approach was conservative debridement of bottom and edges, starting the treatment on the other day. The lesion began to granulate on third infiltration, with contraction of the edges and proliferation of a simple neo-epithelium that eventually became stratified and keratinized. 12 infiltrations sessions were carried out (4 weeks of treatment). Following hospital discharge has satisfactorily.

Example 8

Patient GPJ, 57 years old. The patient has a 12 years evolution of a type-II diabetes mellitus. He bears an ischemic/infectious diabetic foot with no sign of tibial beatings. He suffers a transmetatarsal amputation due to ischemia and necrosis of 4 toes of the right foot. Seven days after the amputation the healing process is halted and the wound edges became cyanotic and devitalized with no evidence of wound repair. The infiltrations are initiated as an alternative maneuver of other surgical interventions. After 9 sessions (3 weeks) the patient had fully re-epithelialized. Upon hospital discharge he has successfully evolved with no complications.

Example 9

Patient DLF, 51 years old, male. A patient with type-II diabetes history and asthma of about 20 years ago. The patient is admitted with a perforating plantar ulcer with severe ischemia and necrosis of the surrounding tissue. The left foot had almost fully demised. The Calcaneus ends up after surgery with an exposed periosteum. Infiltrations are initiated and tried as an alternative of immediate amputation. The only possibility was the uprising of a productive and vascularized granulation tissue suitable to host a skin graft. There were a total of 15 infiltration sessions including the Calcaneus. Upon the $5^{th}$ infiltration the granulation tissue starts to bud. When the 15 infiltration sessions were concluded (5 weeks) grafting was implanted. The patient has successfully evolved. He is currently able to walk by himself.

TABLE 1

| Patient ID | Composition and active principles administered to each patient. |
|---|---|
| | Composition |
| ACDF | EGF (50 mcg/ml) + Rutin (50 mg/ml) |
| ERC | EGF(125 mcg/ml of sodium buffer solution pH 6.5 + 20 mg of O-Raffinose and 10 mg of L-Glycine /ml of buffer) |
| ECS | EGF (125 mcg/ml) + Lidocaine (10 mg/ml) |
| RNP | EGF (10 mcg/ml) + ATP (2.5 mg/ml) |
| ISV | EGF (100 mcg/ml) + GTP (5 mg/ml) |
| RDR | EGF (30 mcg/ml + NAD (25 mg/ml) |
| RGR | EGF(25 mcg/ml) + L-Arginine (10 ng/ml) |
| GPJ | EGF(100 mcg/ml) + Heparin (0.75 U/ml) |
| DLF | EGF (100 mcg/ml of sodium buffer solution pH 6.5 + 10 mg of O-Raffinose, 100 mcg of fibronectin and 15 mg of L-Glycine |

The invention claimed is:

1. A method for enhancing the healing of an ischemic, infectious, or neuropathic diabetic foot ulcer comprising perilesionally injecting said ulcer with a therapeutically effective amount of a pharmaceutical composition comprising epidermal growth factor (EGF), wherein tissue survival is enhanced.

2. The method according to claim 1, wherein said EGF is human EGF.

3. The method according to claim 1, wherein said composition contains from 10 to 1000 micrograms of EGF per milliliter.

4. The method according to claim 1, wherein said composition further comprises from 10 micrograms to 500 milligrams of at least one member of the group consisting of fibronectin, o-raffinose, levan, and polyethyleneimine (PEI).

5. The method according to claim 1, wherein said composition further comprises from 20 to 1000 micrograms per milliliter of rutin.

6. The method according to claim 1, wherein said composition further comprises from 5 to 40 milligrams per milliliter of lidocaine.

7. The method according to claim 1, wherein said composition further comprises from 0.05 to 20 milligrams per milliliter of adenosine triphosphate (ATP) or a salt thereof.

8. The method according to claim 1, wherein said composition further comprises from 1 to 100 milligrams per milliliter of guanosine triphosphate (GTP) or a salt thereof.

9. The method according to claim 1, wherein said composition further comprises from 1 to 130 milligrams per milliliter of nicotinamide.

10. The method according to claim 1, wherein said composition further comprises from 1 to 100 nanograms per milliliter of L-arginine.

11. The method according to claim 1, wherein said composition further comprises from 1 to 10 micrograms per milliliter of a heparin salt.

12. The method according to claim 1, wherein said injections are repeated three or more times.

13. The method according to claim 1, wherein said injections are repeated from 4 to 20 times.

14. The method according to claim 1, wherein said pharmaceutical composition is derived from dry or lyophilized EGF and is reconstituted with water or an aqueous buffer.

15. The method according to claim 1, wherein said injections are made at three or more points distributed along the circumference of the ulcer.

16. The method according to claim 15, wherein said injections are made at 4 to 20 points distributed along the circumference of the ulcer.

17. The method according to claim 1, wherein said injections are made into and around the ulcer so that all the deep bottom surface and edges are flushed with the pharmaceutical composition.

18. The method according to claim 17, wherein said injections are made at 4 to 20 points and the distance between the points is no longer than 1.5 cm.

19. The method according to claim 1, wherein said injections are repeated once per day, once every other day, once every three days, or two to three times per week.

* * * * *

UNITED STATES PATENT AND TRADEMARK OFFICE
CERTIFICATE OF CORRECTION

PATENT NO.         : 7,465,704 B2
APPLICATION NO.    : 10/499457
DATED              : December 16, 2008
INVENTOR(S)        : Berglanga Acosta et al.

It is certified that error appears in the above-identified patent and that said Letters Patent is hereby corrected as shown below:

On the Title Pg

Item (74) Attorney, Agent, or Firm

Now reads:    "Hoffman & Baron, LLP";

Should read:    -- Hoffmann & Baron, LLP --.

Item (57) ABSTRACT, lines 12 and 13

Now reads:    "viability of the is tissues";

Should read:    -- viability of the tissues --.

Column 1, line 6

Now reads:    "PCT/CUO02/00011";

Should read:    -- PCT/CU02/00011 --.

Column 1, line 53

Now reads:    "join. This sustained";

Should read:    -- joint. This sustained --.

Column 1, line 54

Now reads:    "nervous and joins complications,";

Should read:    -- nervous and joints complications, --.

Column 2, line 64

Now reads:    "chronic as venous ulcers";

Should read:    -- chronic and venous ulcers --.

UNITED STATES PATENT AND TRADEMARK OFFICE
CERTIFICATE OF CORRECTION

PATENT NO.        : 7,465,704 B2
APPLICATION NO.   : 10/499457
DATED             : December 16, 2008
INVENTOR(S)       : Berglanga Acosta et al.

It is certified that error appears in the above-identified patent and that said Letters Patent is hereby corrected as shown below:

Column 3, line 22

Now reads:    "sift adjacent tissues";

Should read:    -- soft adjacent tissues --.

Column 3, line 48

Now reads:    "composition by mean of";

Should read:    -- composition by means of --.

Column 3, line 51

Now reads:    "applied by mean of";

Should read:    -- applied by means of --.

Column 4, line 12

Now reads:    "week of treatment, so";

Should read:    -- week of treatment, i.e., --.

Column 4, line 16

Now reads:    "bases. In these patients";

Should read:    -- basis. In these patients --.

Column 4, line 22

Now reads:    "synthesis or by mean of";

Should read:    -- synthesis or by means of --.

Column 4, line 57

Now reads:    "be applied by mean of";

Should read:    -- be applied by means of --.

UNITED STATES PATENT AND TRADEMARK OFFICE
CERTIFICATE OF CORRECTION

PATENT NO. : 7,465,704 B2
APPLICATION NO. : 10/499457
DATED : December 16, 2008
INVENTOR(S) : Berglanga Acosta et al.

It is certified that error appears in the above-identified patent and that said Letters Patent is hereby corrected as shown below:

Column 5, line 6

Now reads: "optimal rage is 8-20 mg/ml.";

Should read: -- optimal range is 8-20 mg/ml. --.

Column 5, line 8

Now reads: "optimal rage is 10-20 mg/ml.";

Should read: -- optimal range is 10-20 mg/ml. --.

Column 5, line 13

Now reads: "It acts screen agent";

Should read: -- It act as a screen agent --.

Column 5, line 65

Now reads: "Among, them a";

Should read: -- Among them, a --.

Column 6, line 39

Now reads: "from hospital. Has shows";

Should read: -- from hospital, showing --.

Column 6, lines 46-47

Now reads: "A minor is transmetatarsal";

Should read: -- A minor transmetatarsal --.

Column 6, line 55

Now reads: "4 cms In depth.";

Should read: -- 4 cms in depth. --.

UNITED STATES PATENT AND TRADEMARK OFFICE
CERTIFICATE OF CORRECTION

PATENT NO.        : 7,465,704 B2
APPLICATION NO.   : 10/499457
DATED             : December 16, 2008
INVENTOR(S)       : Berglanga Acosta et al.

It is certified that error appears in the above-identified patent and that said Letters Patent is hereby corrected as shown below:

Column 7, lines 27-28

Now reads:    "completely re epithelialized";

Should read:    -- completely re-epithelialized --.

Column 7, line 65

Now reads:    "was no required to make";

Should read:    -- was no requirement to make --.

Signed and Sealed this

Twenty-second Day of September, 2009

David J. Kappos
*Director of the United States Patent and Trademark Office*